(12) United States Patent
Koyasu et al.

(10) Patent No.: US 8,524,250 B2
(45) Date of Patent: Sep. 3, 2013

(54) CARRIER

(75) Inventors: Shigeo Koyasu, Tokyo (JP); Shigenori Nagai, Tokyo (JP); Chihiro Sasakawa, Tokyo (JP); Hitomi Mimuro, Tokyo (JP)

(73) Assignee: Keio University, Tokyo (JP)

( * ) Notice: Subject to any disclaimer, the term of this patent is extended or adjusted under 35 U.S.C. 154(b) by 947 days.

(21) Appl. No.: 12/515,507

(22) PCT Filed: Nov. 14, 2007

(86) PCT No.: PCT/JP2007/072102
§ 371 (c)(1),
(2), (4) Date: Sep. 24, 2009

(87) PCT Pub. No.: WO2008/062699
PCT Pub. Date: May 29, 2008

(65) Prior Publication Data
US 2010/0074921 A1    Mar. 25, 2010

(30) Foreign Application Priority Data
Nov. 20, 2006   (JP) .................................. 2006-313217

(51) Int. Cl.
*A61K 39/02* (2006.01)
*G01N 33/53* (2006.01)
*G01N 33/00* (2006.01)

(52) U.S. Cl.
USPC ...... 424/234.1; 424/184.1; 435/7.1; 435/7.24

(58) Field of Classification Search
None
See application file for complete search history.

(56) References Cited

U.S. PATENT DOCUMENTS
2007/0154487 A1   7/2007   Littman et al.

FOREIGN PATENT DOCUMENTS
| EP | 0 862 458 | 9/1998 |
|---|---|---|
| EP | 1 771 204 | 4/2007 |
| JP | 2003-321392 A | 11/2003 |
| JP | 11-514998 | 12/2009 |
| WO | WO 97/13527 | 4/1997 |
| WO | WO 2006/007486 | 1/2006 |

OTHER PUBLICATIONS

Bode et al., "The coccoid forms of *Helicobacter pylori*. Criteria for their viability," *Epidemiol. Infect.* 111: 483-490 (1993).
Pappo et al., "*Helicobacter pylori* infection in immunized mice lacking major histocompatibility complex class I and class II functions," *Infection and Immunity* 67: 337-341 (1999).
Saito et al., "Protective immunity to *Streptococcus mutans* induced by nasal vaccination with surface protein antigen and mutant cholera toxin adjuvant," *The Journal of Infectious Diseases* 183: 823-826 (2001).
Yamamoto et al., "A nontoxic adjuvant for mucosal immunity to pneumococcal surface protein A," *The Journal of Immunology* 161: 4115-4121 (1998).
Chaput et al., "Role of AmiA in the Morphological Transition of *Helicobacter pylori* and in Immune Escape," *PLoS Pathog.* 2(9):0844-0852 (2006).
Dunkley et al., "Protection Against *Helicobacter pylori* Infection by Intestinal Immunisation with a 50/52-kDa Subunit Protein," *FEMS Immunol. Med. Microbiol.* 24(2):221-225 (1999).
Eaton et al., "Murine Spenocytes Induce Severe Gastritis and Delayed-Type Hypersensitivity and Suppress Bacterial Colonization in *Helicobacter pylori*-Infected SCID Mice," *Infect. Immun.* 67(9):4594-4602 (1999).
Lundgren et al., "*Helicobacter pylori*-Specific CD4$^+$ T Cells Home to and Accumulate in the Human *Helicobacter pylori*-Infected Gastric Mucosa," *Infect. Immun.* 73(9):5612-5619 (2005).
Nagai et al., "Role of Peyer's patches in the induction of *Helicobacter pylori*-Induced Gastritis," *Proc. Natl. Acad. Sci. USA* 104(21):8971-8976 (2007).
Naka et al., "Effect of Immunosuppression by FK506 on Development of *Helicobacter pylori*-Induced Gastritis in Mongolian Gerbils," Abstract 3523, *Gastroenterology* 120(5):A-650 (2001).
Wang et al., "Infection of BALB/c A Mice by Spiral and Coccoid Forms of *Helicobacter pylori*," *J. Med. Microbiol.* 46(8):657-663 (1997).
International Search Report for International Application PCT/JP2007/072102, mailed Jan. 22, 2008.

*Primary Examiner* — Nita M Minnifield
(74) *Attorney, Agent, or Firm* — Clark & Elbing LLP

(57) ABSTRACT

The present invention is directed to providing a carrier which can transport a compound to a gut-associated lymphoid tissue efficiently without being degraded or digested. For that purpose, the carrier contains a coccoid cell of a gastric mucosa-damaging spiral bacterium. Preferably, the carrier is orally administered. By making this carrier carry an antigen and orally administering it, a local or a systemic immunological reaction to the antigen can be induced.

5 Claims, 3 Drawing Sheets

CARRIER

CROSS REFERENCE TO RELATED APPLICATIONS

The present application is the U.S. National Stage of International Application No. PCT/JP2007/072102, filed Nov. 14, 2007, which claims the benefit of Japanese Application Ser. No. JP 2006-313217, filed Nov. 20, 2006.

TECHNICAL FIELD

The present invention relates to carriers for transporting compounds to gut-associated lymphoid tissues.

BACKGROUND ART

The immune tissues in the mucosal tissues such as the enteric canal, nasal cavity, oral cavity, respiratory organs, etc., which cover the interface with the external world in the animal body, form an immune system (i.e. mucosal immune system) which is independent of but shares a common mechanism with the immune system (i.e. the systemic immune system), which consists mainly of the spleen and bone marrow.

Among the mucosal tissues, the intestinal tract is not only a digestive organ which digests and absorbs food taken in from outside of the body but also a first line of defense being exposed to various foreign matters from outside of the body. Therefore, the intestinal tract contains abundant immune tissues. The mucosal immune system in the intestinal tract with a surface area spanning about 400 $m^2$, in humans, consists of the gut-associated lymphoid tissues (GALTs), the largest immune tissue in the body, in which 60 to 70% of the body's lymphocytes reside, including Peyer's patches, mesenteric lymph nodes, intraepithelial lymphocytes, cryptopatches, etc.

Especially Peyer's patches located in the lamina propria mucosae in the small intestine play a role as the control tower directing whether immune responses are induced or, conversely, immunological tolerance is induced to various antigens absorbed through intestinal epithelium. Dendritic cells play an important role in the function of Peyer's patches.

As mucosal immune mechanisms as described above have been elucidated one after another, mucosal immune vaccines taking advantage of the mucosal immunity has been developed (Japanese Laid-Open Application No.2003-321392). The mucosal immune vaccine works such that, by transmucosal administration of antigens to the oral cavity or nasal cavity, secretory IgA antibodies are produced in fluid such as saliva from mucosal systems, while blood-serum derived IgG antibodies are produced in fluid such as gingival crevicular fluid from systemic tissues. Thus, the mucosal immune vaccine can induce immune responses both in the mucosal system and in the systemic system by transmucosal administration of antigens.

As an experimental attempt of such immune induction using mucosal immunity, it has been reported that, by nasal administration of a cell membrane protein of *Haemophilus influenzae* to mice as an antigen, IgA antibodies and IgG antibodies were produced in nasal washes and in serum, respectively, and as a result, immune responses were induced both in the mucosal system and in the systemic system (Yamamoto, M. et al. (1998) J. Immune. 161 (8):4115-4121). Further, it has also been reported that by nasal administration of envelope proteins of *Streptococcus* mutants to mice, immune responses were induced both in the mucosal system and in the systemic system (Saito, M. et al. (2001) J. Infect. Dis. 183 (5):823-826). Such mucosal immune vaccines, which are capable of inducing immune responses both in the mucosal system and in the systemic system to pathogenic microorganisms, show promise as a new type of vaccines for clinical application.

DISCLOSURE OF THE INVENTION

Problems to be Solved by the Invention

However, if a substance is administered, for example orally, to exert an effect on a gut-associated lymphoid tissue, it is difficult in many cases to be delivered to the intestinal tract as it is, because it is degraded by gastric acid or digested by digestive enzymes. Even if a substance can reach the intestine, it is not necessarily taken up into the gut-associated lymphoid tissue and can be excreted outside the body as it is.

The present invention has been made in view of the above-mentioned problems for the purpose of providing a carrier which can transport a compound to a gut-associated lymphoid tissue efficiently without being degraded or digested.

Means for Solving the Problems

It is known that *Helicobacter pylori*, a gram-negative spiral bacterium, damages the gastric mucosa, causing gastritis, gastric ulcer, etc. *H. pylori* normally resides in the stomach mucosa in an actively dividing helical form with flagella. However, under the environment with non-optimal conditions, for example, under the anaerobic environment such as in the small intestine or the like, it can survive by transforming into bacterial cells in the coccoid form. Such coccoid cells are considered to be in a kind of "viable but non-culturable" (VNC) state.

It has recently been found that *H. pylori*-specific T cells in the mucosal immune system are involved in the onsets of gastritis and gastric ulcer caused by *H. pylori* (for example, refer to Lundgren, A., et al. (2005) Infect. Immun. 73:5612-5619). However, the stomach itself, which is the inflammatory site, does not have immune tissues and it has not been known at which site in the body the priming of T cells with *H. pylori* occurs. Thus, as a result of assiduous studies, the inventors has found that (1) coccoid *H. pylori* cells are phagocytosed by immune cells highly efficiently and induce immune response of dendritic cells effectively and (2) Peyer's patches in the small intestine, which constitute the gut-associated lymphoid tissues, take up coccoid *H. pylori* cells efficiently and dendritic cells in Peyer's patches phagocytose the captured coccoid cells; and (3) the coccoid *H. pylori* cells induce immune response in Peyer's patches by priming CD4-positive T cells and consequently (4) specific inflammatory immune responses are induced in the stomach. The invention has thus been accomplished.

That is, the carrier according to the present invention is directed to carrying a compound to a gut-associated lymphoid tissue and contains a coccoid cell of a gastric mucosa-damaging spiral bacterium. The gut-associated lymphoid tissue may be a Peyer's patch and the gastric mucosa-damaging spiral bacterium may be *H. pylori*. The compound may be pharmaceutical composition and may further be a pharmaceutical composition acting on a gut-associated lymphoid tissue.

The oral agent according to the present invention contains a compound and a coccoid cell of a gastric mucosa-damaging spiral bacterium. The gastric mucosa-damaging spiral bacterium may be *H. pylori*. The compound may be pharmaceutical composition and may further be a pharmaceutical composition acting on a gut-associated lymphoid tissue.

The inducer according to the present invention induces an immune response by an immune cell of a gut-associated lymphoid tissue to a compound and contains the compound and a coccoid cell of a gastric mucosa-damaging spiral bacterium. The gut-associated lymphoid tissue may be a Peyer's patch and the immune cell may be a dendritic cell. The gastric mucosa-damaging spiral bacterium may be *H. pylori*. The compound may be a protein, and may further be a protein being produced by the spiral bacterium.

The pharmaceutical composition according to the present invention contains a coccoid cell of a gastric mucosa-damaging spiral bacterium as a carrier. The coccoid cell may be a carrier for carrying to a gut-associated lymphoid tissue. The gut-associated lymphoid tissue may be a Peyer's patch and the gastric mucosa-damaging spiral bacterium may be *H. pylori*.

The therapeutic agent according to the present invention is for a gastric inflammatory disease caused by a gastric mucosa-damaging spiral bacterium, the therapeutic agent suppressing cell-mediated immunity in a gut-associated lymphoid tissue. The gastric mucosa-damaging spiral bacterium may be *H. pylori*. The gut-associated lymphoid tissue may be a Peyer's patch. Further, the therapeutic agent according to the present invention may contain a coccoid cell of a gastric mucosa-damaging spiral bacterium.

BEST MODE FOR CARRYING OUT THE INVENTION

Figure 1:
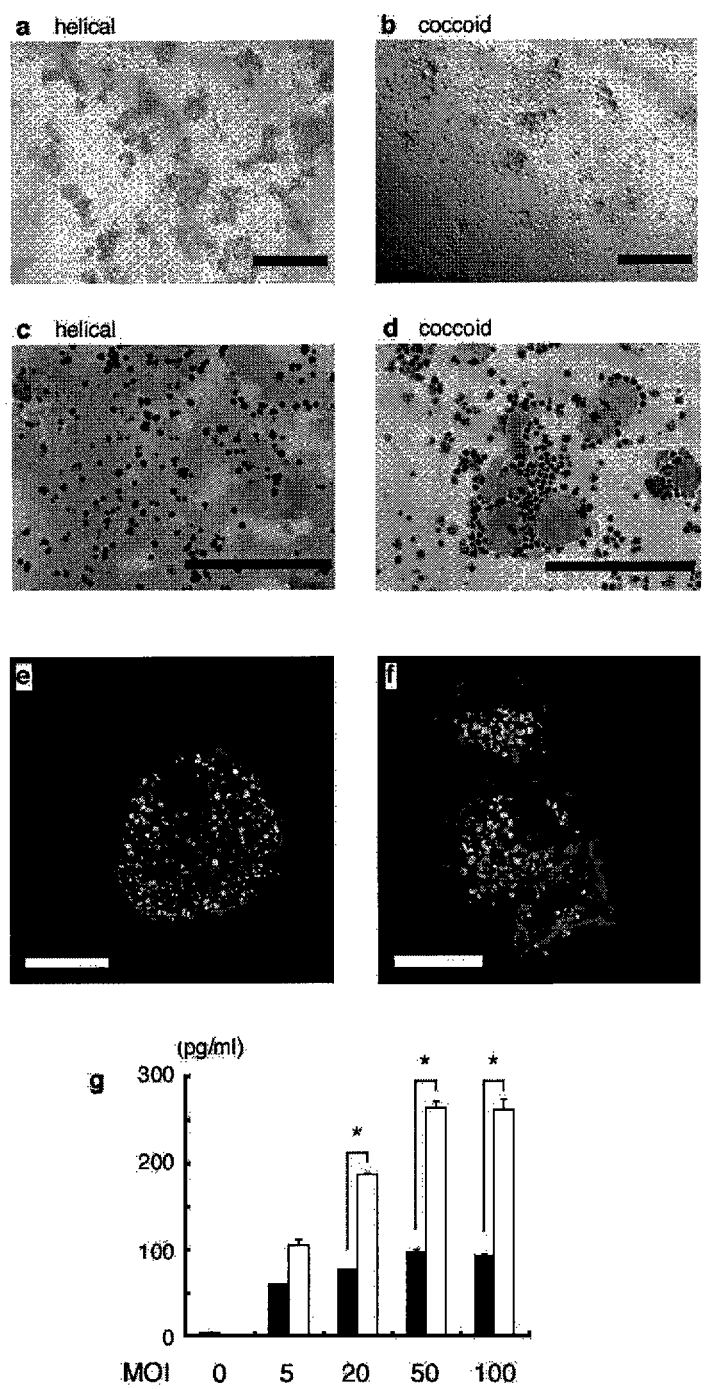
FIG. 1 shows the results obtained by infection of *H. pylori* to cultured cells in the Example according to the present invention. (a) to (d) are photographs showing microscopic observation of spleen cells unstained on culture plates (a and b) or stained with hematoxylin and eosin on coverslips (c and d), which are infected with helical cells (a, c) or coccoid cells (c, d) of *H. pylori*. (e) and (f) are photographs showing the fluorescence microscopic observation of cultured spleen cells (e) or BMDCs (f), which are infected with coccoid *H. pylori* cells and nuclear-stained as well as immunostained with anti-*H. pylori* antiserum. (g) is a bar graph plotting the measured amount of IL-12p70 contained in the culture medium in which BMDCs were infected with helical cells (black bars) or coccoid cells (white bars) of *H. pylori* at 0 to 100 MOI.

Unless otherwise explained, methods described in standard sets of protocols such as J. Sambrook and E. F. Fritsch & T. Maniatis (Ed.), "Molecular Cloning, a Laboratory Manual (3rd edition), Cold Spring Harbor Press and Cold Spring Harbor, N.Y. (1989); and F. M. Ausubel, R. Brent, R. E. Kingston, D. D. Moore, J. G. Seidman, J. A. Smith, and K. Struhl (Ed.), "Current Protocols in Molecular Biology," John Wiley & Sons Ltd., or alternatively, their modified/changed methods are used. When using commercial reagent kits and measuring apparatus, unless otherwise explained, protocols attached to them are used.

The object, characteristics, and advantages of the present invention as well as the idea thereof will be apparent to those skilled in the art from the descriptions given herein. It is to be understood that the embodiments and specific examples of the invention described herein below are to be taken as preferred examples of the present invention. These descriptions are only for illustrative and explanatory purposes and are not intended to limit the invention to these embodiments or examples. It is further apparent to those skilled in the art that various changes and modifications may be made based on the descriptions given herein within the intent and scope of the present invention disclosed herein.

---Transport of a Compound by the Carrier---

The present invention provides a vehicle, i.e., a carrier for transporting a compound efficiently to a gut-associated lymphoid tissue.

The compound to be transported by the carrier according to the present invention may be a low molecule, or may be a biomacromolecule such as a nucleic acid and a protein. Alternatively, the compound may be a microorganism such as a bacterium or a virus, or part thereof, but a compound exerting its effect in a gut-associated lymphoid tissue is preferred.

The site to which the carrier according to the present invention transports a compound is a gut-associated lymphoid tissue (GALT) including Peyer's patches in the small intestine. Coccoid cells of the spiral bacterium used as the carrier according to the present invention reach as far as Peyer's patches when being orally administered and is taken up effectively by phagocytosis of dendritic cells at the Peyer's patch. Therefore, by using the carrier according to the present invention, a compound can be efficiently transported to Peyer's patches and their adjacent gut-associated lymphoid tissue and thus the compound can be used for the present invention as an active ingredient of a topical agent for a gut-associated lymphoid tissue. Therefore, it is preferred that the compound to be transported by the carrier according to the present invention exerts its effect by reaching a gut-associated lymphoid tissue, but it does not need to act in a gut-associated lymphoid tissue itself.

Since a compound, which exerts its effect by acting locally on a gut-associated lymphoid tissue, is efficiently transported to the tissue, the scope of its effect is limited to a gut-associated lymphoid tissue and/or its vicinity. For an example, if a compound has immunogenicity, when transported by the carrier according to the present invention, it is taken up by dendritic cells in Peyer's patches of the gut-associated lymphoid tissue and is presented to CD4-positive T cells. For another example, if a compound has immunosuppressive activity, when transported to a gut-associated lymphoid tissue using the carrier according to the present invention, it can act on a gut-associated lymphoid tissue, thereby suppressing mucosal immune responses. Furthermore, the compound may have other functions than those described above, which are effective on gut-associated lymphoid tissues. For example, if the compound has antimicrobial activity, it can be transported by the carrier according to the present invention as an active ingredient of an antimicrobial agent on a gut-associated lymphoid tissue.

Meanwhile, the site which the effect produced by the transported compound reaches may differ depending on the action of the compound. For example, when the transported compound has an action of specifically regulating immune responses, i.e., either inducing or suppressing immune responses, the scope of the effect is not limited to a gut-associated lymphoid tissue. That is, as is observed, for example, in the function of inducing inflammatory responses by H. pylori in the stomach, when a compound serving as an immunogen is once taken up by dendritic cells and presented to CD4-positive T cells, the primed T cells are transported throughout the body via the circulatory system. Therefore, the specific immune response reaction made by the transported compound can be induced at any site in the body where the substance serving as an immunogen is present, whether in the mucosal immunity or the systemic immunity.

A representative example of a gastric mucosa-damaging spiral bacterium which can be used for the present invention is H. pylori of the genus Helicobacter, a bacteria associated with human gastritis and gastric ulcer. In addition, it is known that, among spiral bacteria of the genus Helicobacter, for example, H. felis, H. mustelae, H. rodentium, H. hepaticus, etc. can induce inflammation by residing in the gastric mucosa and can assume a coccoid form. Each of these species has been confirmed to infect cats and/or dogs, and is used in animal experiments using mice and ferrets. Therefore, these bacteria can also be used for the present invention, like H. pylori, by using them to a suitable mammal to which they can infect.

---Use of a Spiral Bacterium as a Carrier---

The present invention provides a carrier for carrying a compound to a gut-associated lymphoid tissue by taking advantage of the phenomenon in which coccoid cells of a spiral bacterium are efficiently taken up into the gut-associated lymphoid tissue. For that purpose, either such coccoid cells themselves or processed products of such cells are used for the carrier according to the present invention. Spiral bacteria can easily be transformed to a coccoid form by growing them in culture under an optimal condition and then changing the culture condition to a condition unsuitable for growth of bacteria, for example, an anaerobic condition. Once spiral bacteria have transformed to a coccoid form, they lose their ability to form colonies (the VNC state) and becomes more stable. Thus, it is appropriate from the viewpoint of safety and ease of handling to use coccoid cells as a carrier.

Coccoid cells may be used as they are when they are in the VNC state or may be processed before use if properties enabling transportation to a gut-associated lymphoid tissue can be retained. For example, since it does not matter whether the spiral bacteria are dead or alive, a processed product of coccoid cells may be used, such as killed cells or cells obtained either by attenuating or by inactivating viable cells after they have transformed to coccoid cells. For such an attenuation or inactivation, general methods, such as radiation of ultraviolet rays or electron beams, drying, heating, or the like may be used. Further, other processed products of coccoid cells can be used, which have been obtained by decreasing the antigenicity inherent in a spiral bacterium by treatment of inactivating the antigens on the surface of bacterial cells, such as, for example, enzymatic hydrolysis treatment. Such treatment for decreasing the antigenicity is preferable, because it can circumvent the side effect of inducing immunological reaction to the spiral bacterium, which can possibly occur when coccoid cells themselves are administered as a carrier.

As the method for administering a compound using the carrier according to the present invention, oral administration is preferred, which can be noninvasively performed. Coccoid cells of a spiral bacterium are highly stable and, for example, resistant to degradation by acids such as gastric acid or digestion by digestive enzyme. Therefore, using coccoid cells as a carrier, a compound can be transported to the intestines, without being degraded or digested and in a noninvasive manner, simply by being orally administered. However, some other mode of administration can also be used as long as it enables a compound to reach to a gut-associated lymphoid tissue; for example, a compound may be directly administered to the stomach or intestines by means of injection or catheter.

The dosage forms for administering a compound using the carrier according to the present invention is not limited as long as coccoid cells or a processed product of coccoid cells as mentioned above can be contained. Further, for oral administration, dosage forms suitable for oral administration are preferred; for example, tablets, capsules, granules, powders, syrups, etc. may be used. Moreover, the numbers of administrations or intervals between administrations is not particularly limited, but can be appropriately adjusted depending on the degree of the action expected and on the increase or decrease in actual effect. Furthermore, these dosage forms may be administered independently or in combination with other agents.

The compound administered by the carrier according to the present invention is contained in a form suitable for transportation to a gut-associated lymphoid tissue in the above-mentioned dosage forms. For that purpose, it is preferred that a compound is bound onto the surface of the carrier or contained inside it so as to be stably held in the dosage form. The procedure of binding or containing a compound in this manner may be performed either before or after forming and/or processing the aforementioned coccoid cells. For example, a compound may be bound onto the surface by being added to coccoid cells or a processed product of coccoid cells of a spiral bacterium. A compound may be bound directly or via a crosslinker to the surface of coccoid cells or a processed product of coccoid cells.

Meanwhile, when a compound is contained inside the carrier, if the compound is permeable, it may be added to coccoid cells or a processed product of coccoid cells of a spiral bacterium so that the compound permeate from the surface to the inside, thereby being stably carried inside. Alternatively, the compound may be taken up inside by taking advantage of the import action by spiral bacteria. It is preferred that a compound is contained inside bacterial cells, because degradation of the compound by gastric acid or its digestion by digestive enzymes, which could occur in the case of binding the compound onto the surface, can be circumvented; and because an undesirable effect possibly occurring when the compound is halfway to a gut-associated lymphoid tissue (e.g., damaging the esophagus or the stomach) can be circumvented.

When the compound is a biological molecule, such as a nucleic acid, a protein, or a peptide, it may be added to the carrier afterward as mentioned above, or alternatively may be produced by the spiral bacterium itself. For example, while culturing a spiral bacterium, by expressing the biological molecule in bacterial cells using the gene expression system of the spiral bacterium and then changing the culture condition to transform the cells into coccoid cells, the coccoid cells can be used for the present invention as a carrier carrying such a biological molecule.

---Methods for Using the Carrier---

The carrier according to the present invention enables a compound to be taken up efficiently into a gut-associated lymphoid tissue. By taking advantage of this phenomenon, the following uses of the carriers are possible.

First, the carrier can be used as an inducer which induces immune responses to a compound by immune cells of the gut-associated lymphoid tissue. When $H.$ $pylori$ is taken up into Peyer's patches, dendritic cells are activated and CD4-positive T cells are primed, resulting in induction of specific inflammatory immune responses in the stomach. Moreover, immune responses in the mucosal system can be induced by transmucosally administrating an antigen as described above. Therefore, immune responses by immune cells of a gut-associated lymphoid tissue can be induced by administrating a compound of interest to the gut-associated lymphoid tissue using this carrier.

Similarly, since systemic immune responses can be induced by transmucosally administrating an antigen, a mucosal immunity vaccine can be provided using coccoid cells of a gastric mucosa-damaging spiral bacterium as a carrier. Preferably, this vaccine targets not only compounds but also microorganisms, viruses, or part thereof. In addition, cancer-specific antigens used for cancer vaccines and the like may also be targeted.

Inflammation associated with a gastric mucosa-damaging spiral bacterium in the gastric mucosa is caused by the gastric mucosa-damaging spiral bacterium inducing immunity in Peyer's patches. Therefore, by making the carrier according to the present invention carry a compound exerting an immunosuppressive effect in a gut-associated lymphoid tissue, inflammatory immunity associated with a gastric mucosa-damaging spiral bacterium can be suppressed, thereby making it possible to provide pharmaceutical compositions serving as therapeutic agents for gastric inflammatory diseases associated with gastric mucosa-damaging spiral bacteria.

---Therapeutic Agents for Inflammatory Diseases Associated With Gastric Mucosa-Damaging Spiral Bacteria---

As will be shown in Examples, inflammations associated with gastric mucosa-damaging spiral bacteria in the gastric mucosa are caused by the bacteria inducing immunity in Peyer's patches. Therefore, by suppressing a certain phase in this process, it becomes possible to treat gastric inflammatory disease associated with gastric mucosa-damaging spiral bacteria. This is the first-ever therapeutic method for inflammation associated with gastric mucosa-damaging spiral bacteria, which is targeted at the small intestine.

First and foremost, since coccoid cells of a gastric mucosa-damaging spiral bacterium are taken up into Peyer's patches, the gastric inflammation associated with the spiral bacterium can be treated and/or prevented by inhibiting transformation of the bacterium from the helical form to the coccoid form. Also, by inhibiting uptake of coccoid cells into Peyer's patches, gastric inflammation associated with the spiral bacterium can be treated and/or prevented. Moreover, even if coccoid cells have been taken up into Peyer's patches, inflammation will not occur if inflammatory cell-mediated immunity is not induced. Therefore, by suppressing immune responses in Peyer's patches, gastric inflammation associated with the spiral bacterium can be treated and/or prevented.

For example, in order to suppress cell-mediated immunity in the gut-associated lymphoid tissues including Peyer's patches, administration of an immunosuppressive agent to a gut-associated lymphoid tissue is conceived. This immunosuppressive agent only requires its function of suppressing immune responses caused by coccoid cells in a gut-associated lymphoid tissue. Examples of such an immunosuppressive agent include Imuran (azathioprine preparation), Cyclosporin A, Tacrolimus (FK506), etc.

Mode of administration is not particularly limited, but oral administration is preferred from the viewpoint of noninvasiveness.

EXAMPLE

Hereinafter, the present invention will be explained in more detail with reference to an Example and Drawings.

---Phagocytosis of $H.$ $pylori$ by Immune Cells---

First, phagocytic ability of spleen cells and bone marrow-derived dendritic cells (BMDCs) on helical or coccoid cells of $H.$ $pylori$ was examined. Further, immune responses occurring when BMDCs endocytose helical or coccoid cells of $H.$ $pylori$ were examined by measuring the amount of IL-12 secreted.

[Preparation of $H.$ $pylori$ Cells]

SS1, a mouse-adapted strain of $H.$ $pylori$ that was isolated from human, was cultured on 5% sheep blood agar plates for 2 days, and then grown in Brucella broth with 5% FCS overnight at 37° C. under the microaerobic condition with shaking to obtain helical cells. When coccoid cells were prepared, SS1 was cultured on 5% sheep blood agar plates under the microaerobic condition at 37° C. for 3 days and subsequently under the anaerobic condition at 37° C. for 7 days.

[Preparation of Spleen Cells]

The spleen of C57BL/6 wild-type mice was harvested, crushed to squeeze spleen cells. The cells were collected and centrifuged, and then red blood cells were lysed with Ack buffer. The cells were washed with phosphate buffer solution and suspended in a medium to obtain a spleen cell preparation.

[Preparation of BMDCs]

Cells isolated from the bone marrow of C57BL/6 wild-type mice (Clea Japan) were cultured on 6-well culture plates using RPMI medium containing 10% fetal bovine serum and 10 ng/ml GM-CSF. The culture medium was exchanged every other day to remove granular cells. On culture day 6, cells loosely adherent to the plate surface were collected by gentle pipetting. CD11c-positive cells were isolated using Anti-CD11c antibody-conjugated N418 microbeads and the AutoMACS cell separator (Miltenyi Biotech) to obtain BMDCs.

[In Vitro Infection Experiment]

Cultured naive spleen cells were infected with $H.$ $pylori$ by the addition of helical cells and coccoid cells of $H.$ $pylori$ SS1 at 20 MOI (multiplicity of infection), followed by co-culture at 37° C. for 3 days on culture plates or coverslips. To BMDCs, coccoid $H.$ $pylori$ SS1 cells were added at 100 MOI and they were co-cultured at 37° C. for 1 h. Cells obtained were smeared on slide glasses, fixed in 10% neutral formalin, permeabilized with 0.1% Triton X-100, and were stained with hematoxylin-eosin or the combination of DAPI staining, phalloidin staining, and immunostaining with anti-$H.$ $pylori$ antibody (Biomeda). The samples were observed under the microscope.

[Measurement of IL-12 Producing Ability]

After incubation in 24-well culture plates for 1 h, $5 \times 10^5$ BMDCs were infected with $H.$ $pylori$ SS1 at 0 to 100 MOI. After 1 h, extracellular bacteria were cleared by adding 50 µg/ml gentamycin, and continued incubation for 20 h. The amount of IL-12p70 secreted in the conditioned medium was measured using an ELISA kit (Invitrogen) containing anti-IL-12p70 antibody.
[Results]

When helical cells or coccoid cells of *H. pylori* were added to spleen cells, coccoid cells formed mononuclear giant cells with a diameter of 30 to 50 nm (FIG. 1*b, d*), but helical cells did not (FIG. 1*a, c*). Many bacterial cells were observed inside and in the vicinity of the giant cells formed as a result of the addition of the coccoid cells (as shown by many small spots in FIG. 1*b, d*). BMDCs to which coccoid cells were added endocytosed many bacterial cells (shown as small light spots in FIG. 1*e, b*).

Meanwhile, IL-12 production by BMDCs to which helical cells or coccoid cells were added at 0 to 100 MOI was induced more effectively by coccoid cells than by helical cells (FIG. 1*g*).

Thus, coccoid cells of *H. pylori* were endocytosed by immune cells more efficiently, and induced immune responses of dendritic cells more effectively than helical cells.

---Uptake of Coccoid *H. pylori* Cells Into Peyer'S Patches of the Small Intestine---

Further, uptake of coccoid *H. pylori* cells to Peyer's patches was examined by inoculating the mouse small intestine with coccoid *H. pylori* cells.
[In Situ Inoculation Experiment into Mouse Small Intestinal Loop]

C57BL/6 wild-type mice (6-week-old females) were anaesthetized. An 4-cm-long piece of the small intestine containing one or two Peyer's patches was ligated at both ends with surgical thread. *H. pylori* SS1 ($1 \times 10^9$ cfu) suspended in 0.2 ml of saline was inoculated into the loop. After certain periods, the Peyer's patches were removed, extensively washed with PBS, and fixed in 4% paraformaldehyde in PBS. Paraffin-embedded sections were prepared and the subepithelial dome (SED) of Peyer's patches was immunostained with anti-*pylori* antibody (Biomeda) or the anti-CD11c monoclonal antibody (Becton Dickinson). The samples were observed under the fluorescence microscope.
[Results]

Figure 2:
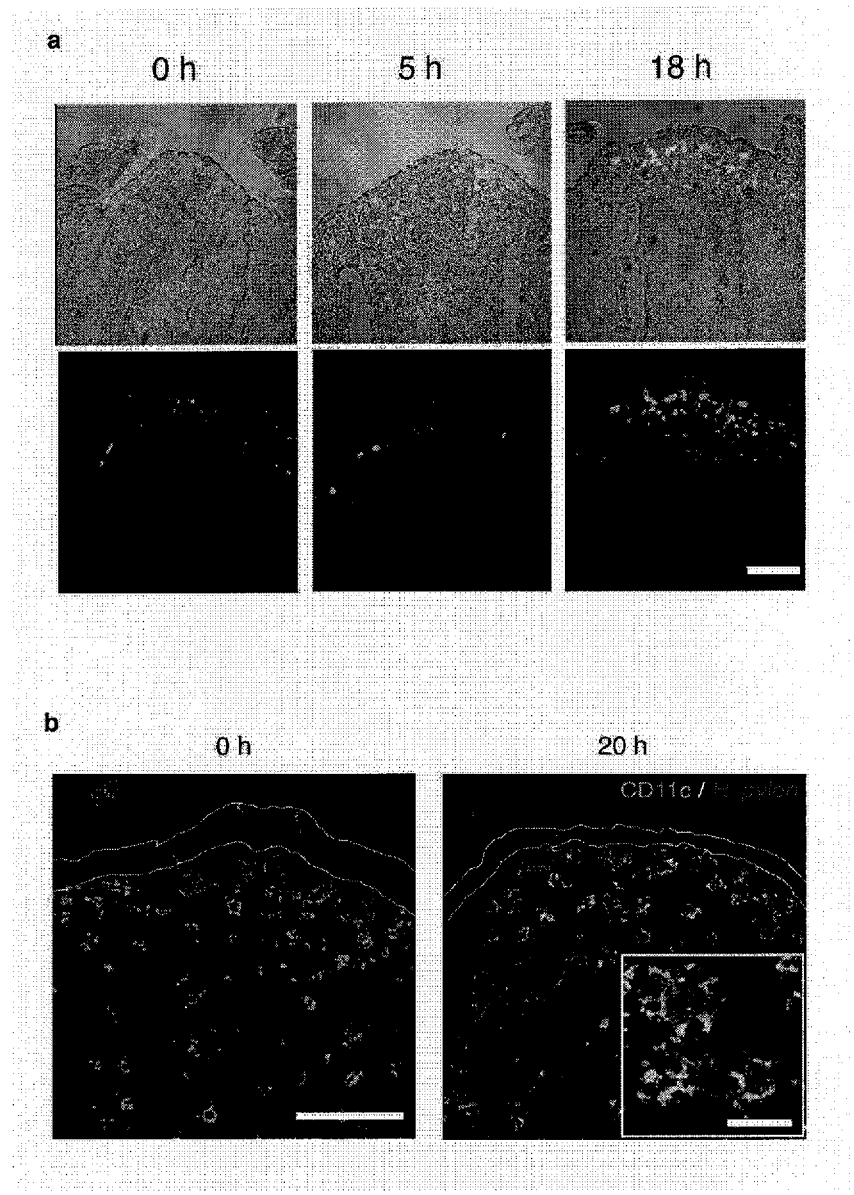
FIG. 2 shows the results obtained by infection of *H. pylori* to the small intestine of mice in the Example according to the present invention. (a) is photographs showing the fluorescence microscopic observation of Peyer's patches in the small intestine immunostained with the anti-*H. pylori* antiserum 0, 5, and 18 hours, from left to right, after the inoculation with *H. pylori*. The upper panels show the bright-field images and the lower panels show the dark field images. (b) is photographs showing the fluorescence microscopic observation of Peyer's patches in the small intestine immunostained with the anti-*H. pylori* antiserum and anti-CD11c antibody immediately (left) and 20 hours (right) after the inoculation with *H. pylori*. The bottom-right inset shows a magnified image of a part of the whole image, indicating that *H. pylori* cells and CD11c-positive dendritic cells are co-stained.

In the mouse small intestinal loop inoculated with coccoid *H. pylori* cells, the uptake of *H. pylori* into the subepithelial dome (SED) region of Peyer's patches was promoted in a time-dependent manner within 18 h after inoculation (FIG. 2*a*). At 20 h after inoculation, by double immunofluorescence staining with anti-*H. pylori* antiserum and anti-CD11c monoclonal antibody, *H. pylori* and CD11-positive dendritic cells were co-stained (FIG. 2*b*).

Thus, coccoid *H. pylori* cells were taken up into Peyer's patches of the intestinal tract and Peyer's patch dendritic cells endocytosed the captured coccoid *H. pylori* cells efficiently. This result indicates that a coccoid *H. pylori* cell is useful as a carrier for transporting a compound to Peyer's patches and that a compound transported by this carrier induces immune responses by dendritic cells.

---Induction of Mucosal Immunity by T Cells Primed With *H. Pylori*---

Next, CD4-positive T cells isolated from *H. pylori*-infected or uninfected mice were adoptively transferred to Peyer's patch/immune cell-deficient mice infected with *H. pylori* and the effect of *H. pylori* clearance in T cells transferred in the mice subjected to transfer was examined.
[Priming of T Cells With *H. pylori* Antigens]

The spleen, mesenteric lymph nodes, and Peyer's patches were removed from *H. pylori*-uninfected wild-type mice (C57BL/6 strain), and CD4-positive T cell were isolated using CD4 microbeads and the AutoMACS cell separator (Miltenyi Biotech) to obtain naive T cells. Meanwhile, 0.15 ml (1 to $2 \times 10^8$ cfu) of *H. pylori* SS1 culture in log-phase was intragastrically administered to the wild-type mice with a sonde Mice were infected with *H. pylori* as they were housed for eight weeks. From these *H. pylori*-infected mice, the spleen, mesenteric lymph nodes, and Peyer's patches were removed, and CD4 -positive T cells were isolated in the same manner described above to obtain *H. pylori*-primed T cells.
[Experiment of Adoptive Transfer of T Cells]

C57BL/6 wild-type mice or (γc)-Rag2 double knockout immunodeficient mice derived from C57BL/6 (Taconic, Germantown, N.Y.) were infected with *H. pylori* by intragastrically administering *H. pylori* SS1 with a sonde. These infected mice were housed for eight more weeks and used as host mice. The aforementioned naive or primed T cells were adoptively transferred to the host mice by intravenous injection ($5 \times 10^6$ cells/mouse for spleen and mesenteric lymph node-derived T cells; $5 \times 10^5$ cells/mouse for Peyer's patch-derived T cells) and the mice were housed continuously.
[Measurement of Effect of *H. pylori* Clearance]

From each of the mice subjected to adoptive transfer of the aforementioned cells, the stomach was removed 8 weeks after transfer, which was sectioned into two portions along the lesser curvature. The one portion was homogenized, and the number of bacteria infected per unit tissue weight of the stomach was determined by counting by the plate dilution method.
[Results]

(γc)-Rag2 double knockout immunodeficient mice lack differentiation ability of B and a T cells as well as Peyer's patches. For that reason, when naive T cells were adoptively transferred to (γc)-Rag2 double knockout immunodeficient mice infected with *H. pylori*, inflammation could not be induced and clearance of *H. pylori* in the stomach did not take place (Table 1). However, when CD4-positive T cells derived from spleen, mesenteric lymph nodes (mLNs), Peyer's patches (PPs) in mice infected with *H. pylori* were adoptively transferred, *H. pylori* of the stomach of (γc)-Rag2 double knockout immunodeficient mice was cleared in all of three cases. In particular, Peyer's patch-derived T cells had an extremely strong clearance effect although their number was smaller than that of spleen or mesenteric lymph node-derived T cells.

TABLE 1

*H. pylori* clearance by adoptive transfer of T cells

| Host mouse | Number | Cells transferred | Bacterial colonization (cfu/g tissue × $10^{-6}$) |
|---|---|---|---|
| Wild type | 7 | None | 2.2 ± 1.3 |
| γc-Rag doube KO | 6 | Naïve T cells from spleen | 18 ± 11 |
| γc-Rag doube KO | 6 | Primed T cells from spleen | 0.22 ± 0.39 |
| γc-Rag doube KO | 3 | Primed T cells from mLN | 0.88 ± 0.78 |
| γc-Rag doube KO | 3 | Primed T cells from PPs | <0.01 |
| γc-Rag doube KO | 3 | Primed T cells by coccoid form | 1.8 ± 1.6 |

Thus, T cells in the systemic immune system and mucosal immune system induced immunological reaction to *H. pylori* by being primed with *H. pylori* antigens. Above all, primed T cells derived from Peyer's patches, a gut-associated lymphoid tissue, induced strong immune responses to *H. pylori*.

This result indicates that, by providing Peyer's patches with antigens, not only local immunity but also systemic immunity is induced, confirming that introduction of antigens into Peyer's patches using *H. pylori* is effective as vaccination of mucosal immunity.

---Induction of Gastritis by T cells Primed With *H. pylori*---

CD4-positive T cells primed with coccoid *H. pylori* cells were transplanted to Peyer's patch/immune cell-deficient mice infected with *H. pylori* and inflammation of the stomach in the transplanted mice was examined.

[Adoptive Transfer Experiment]

(γc)-Rag2 double knockout immunodeficient mice were infected with *H. pylori* by intragastrically administering helical *H. pylori* SS1 cells with a sonde. These infected mice were housed for 2 months and used as host mice. Likewise, coccoid *H. pylori* cells were intragastrically administered to wild-type mice in the same manner and *H. pylori*-primed CD4-positive T cells were isolated from the spleen in the same manner as described above. The *H. pylori*-primed T cells thus obtained were adoptively transferred to the aforementioned host mice in the same manner as described above. The stomach was removed from the mice two months after transfer and sectioned transversely, and frozen sections as well as paraffin sections were prepared. The sections were subjected to hematoxylin/eosin staining or chloroacetic acid esterase staining and observed under the microscope.

[Results]

Figure 3:
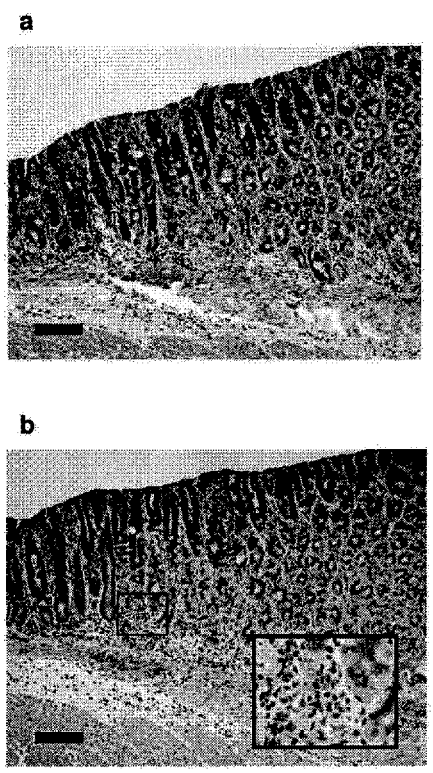
FIG. 3 shows the results obtained by adoptive transfer of CD4-positive T cells primed with coccoid *H. pylori* cells into immunodeficient mice in the Example according to the present invention. (a) and (b) are photographs showing microscopic observation of eosin-stained (a) or Chloroacetic-acid esterase-stained (b) stomach sections that were made 2 months after the transfer of *H. pylori*-primed T cells. The bottom-right inset in (b) shows a magnified image of the squared region in the whole image, indicating neutrophils and mast cells with large numbers of spots.

Since (γc)-Rag2 double knockout immunodeficient mice infected with *H. pylori* lack in Peyer's patches and immune cells, they did not develop gastritis; however, when T cells primed with coccoid *H. pylori* cells were transplanted into the mice, the T cells transplanted caused severe gastritis (FIG. 3).

These findings suggest that coccoid *H. pylori* cells induce responses in the mucosal immune system, by being taken up into Peyer's patches in the gut-associated lymphoid tissues and endocytosed by dendritic cells to prime T cells, thereby aggravating *H. pylori*-associated gastritis. Therefore, by suppressing a certain stage in this process, it becomes possible to treat gastric inflammatory disease associated with a gastric mucosa-damaging spiral bacterium. For example, drugs which suppress cell-mediated immunity in gut-associated lymphoid tissues are useful as therapeutic agents for gastric inflammatory diseases associated with a gastric mucosa-damaging spiral bacterium.

Industrial Applicability

The present invention can provide a carrier which efficiently transports a compound to a gut-associated lymphoid tissue.

The invention claimed is:

1. A method for carrying a compound to a gut-associated lymphoid tissue of an animal, comprising a step of administering the compound to the animal, using a coccoid cell of a gastric mucosa-damaging spiral bacterium as a carrier of the compound.

2. The method of claim 1, wherein the gut-associated lymphoid tissue is a Peyer's patch.

3. The method of claim 1, wherein the gastric mucosa-damaging spiral bacterium is H. pylori.

4. The method of claim 1, wherein the compound is a pharmaceutical composition.

5. The method of claim 4, wherein the pharmaceutical composition acts on a gut-associated lymphoid tissue.

* * * * *